(12) United States Patent
Witte

(10) Patent No.: US 8,347,768 B2
(45) Date of Patent: Jan. 8, 2013

(54) SCREWDRIVER FOR AN INNER PROFILE SCREW

(75) Inventor: Peter Witte, Kiel (DE)

(73) Assignee: Stryker Trauma GmbH (DE)

( * ) Notice: Subject to any disclaimer, the term of this patent is extended or adjusted under 35 U.S.C. 154(b) by 512 days.

(21) Appl. No.: 11/988,512

(22) PCT Filed: Jul. 8, 2006

(86) PCT No.: PCT/DE2006/001185
§ 371 (c)(1),
(2), (4) Date: Mar. 18, 2009

(87) PCT Pub. No.: WO2007/006282
PCT Pub. Date: Jan. 18, 2007

(65) Prior Publication Data
US 2009/0211412 A1  Aug. 27, 2009

(30) Foreign Application Priority Data

Jul. 13, 2005 (DE) .................... 20 2005 011 010 U
Dec. 16, 2005 (DE) .................... 20 2005 019 646 U

(51) Int. Cl.
*B25B 23/02* (2006.01)
(52) U.S. Cl. ............................................. 81/443; 81/442
(58) Field of Classification Search ............. 81/442–450
See application file for complete search history.

(56) References Cited

U.S. PATENT DOCUMENTS

| 518,472 | A | * | 4/1894 | Snyder ............................ 81/448 |
| 1,011,227 | A | * | 12/1911 | Mitchell ........................ 279/36 |
| 1,131,990 | A | * | 3/1915 | Bocorselski ................... 279/36 |
| 2,775,913 | A | * | 1/1957 | Deliso ............................ 81/448 |
| 3,894,450 | A | * | 7/1975 | Hill et al. ...................... 81/448 |
| 4,078,593 | A | * | 3/1978 | Benitz ............................ 81/443 |
| 4,389,913 | A | * | 6/1983 | Drouin et al. ................ 81/53.2 |
| 4,553,455 | A | * | 11/1985 | Wilcox et al. ................ 81/443 |
| 4,557,676 | A | | 12/1985 | Petersen et al. |
| 4,565,662 | A | | 1/1986 | Mansson et al. |
| 4,779,494 | A | | 10/1988 | Quach |
| 6,973,860 | B2 | * | 12/2005 | Nish .............................. 81/443 |

FOREIGN PATENT DOCUMENTS

| AT | 166083 | 8/1986 |
| CN | 2080444 U | 7/1991 |
| DE | 1866996 U | 12/1962 |
| GB | 2389551 | 12/2003 |
| JP | 59-140170 A | 8/1984 |

OTHER PUBLICATIONS

International Search Report, PCT/DE2006/001185.

* cited by examiner

*Primary Examiner* — Robert Scruggs
(74) *Attorney, Agent, or Firm* — Lerner, David, Littenberg, Krumholz & Mentlik, LLP

(57) ABSTRACT

A screw driver for a screw having a drive socket having an axially extending shaft with a bifurcated tip, the tip having a cross-sectional profile for insertion into a cross-sectional profile of the screw socket. The shaft has a tapered section adjacent the bifurcated tip. A bushing is mounted on an outer surface of the shaft for axial movement therealong. The bushing has inwardly extending protrusions for engaging the tapered section on the shaft upon movement in the axial direction along the shaft in a direction. away from the tip. This allows the selective capture or release of the screw by the shaft tip by axial movement of the bushing away from and towards the shaft distal tip.

8 Claims, 2 Drawing Sheets

SCREWDRIVER FOR AN INNER PROFILE SCREW

CROSS-REFERENCE to RELATED APPLICATIONS

The present application is a national phase entry under 35 U.S.C. §371 of International Application No. PCT/DE2006/001185 filed Jul. 8, 2006, which claims priority from German Patent Application No. 202005011010.8 filed Jul. 13, 2005 and German Patent Application No. 202005019646.0 filed Dec. 16, 2005, all of which are incorporated herein by reference.

BACKGROUND OF THE INVENTION

The invention concerns a screwdriver for an inner profile screw with a shaft and an outer profile head designed to correspond to the inner profile recess of the inner profile screw, in particular for use in connection with the surgical implantation of an implant into the body of a human being.

For example, during the implantation of a splint to be screwed to a bone, profile screws are normally used in conjunction with a screwdriver whose head is provided with an outer profile head which engages with the screw inner profile recess. Before screwing, it is important that the inner profile screw is held in such a way to the head of the screwdriver that it can not slip out.

From DE 1 866 996 such a screwdriver is known, which works in conjunction with a hollow head screw, and whose shaft is split into two half-sections by a longitudinal gap, which splay themselves apart due to their spring action, and so jam themselves into the screw head. From U.S. Pat. No. 4,779,494 a similarly developed screwdriver is known, with which the non-forcedly separated sections of the shaft are aligned by pushing a bushing forward.

In the case of prior art screwdrivers, they produce a clamping force, with which the section of the shaft is pressed against the inner profile recess in the inner profile screw, from the elasticity of the material of the shaft pushed back into the splayed position. The clamping force is therefore not precisely defined, but is dependent on tolerances (also in respect of the inner profile recess of the screw).

SUMMARY OF THE INVENTION

The invention is based on the task to create a screwdriver, which is simply developed and manufactured, in particular a screwdriver, which applies a reproducible clamping force, independent of the tolerance of the inner profile recess of the screw.

According to an exemplary embodiment, a screwdriver for an inner profile screw is developed, which comprises a shaft and an outer tip or head profile designed in a manner which corresponds to the inner profile recess of the inner profile screw, whereby the distal region of the shaft with the outer head profile is formed in a split manner, and a bushing receives the shaft and can be moved in relation to it, whereby at least the one of the sections of the shaft arising from the split is provided with an oblique contact member and the bushing is provided with a contact ring which acts upon the oblique contact member(s), whereby through a movement of the bushing relative to the shaft, the section of the shaft provided with the oblique contact member is split off from the other part, by clamping the inner profile recess with the outer profile head.

According to a further exemplary embodiment, a screwdriver for an inner profile screw is developed, which comprises a shaft and an outer head profile designed in a manner which corresponds to the inner profile recess of the inner profile screw, whereby the screwdriver is designed with a screwable bushing that receives the shaft made from an elastic material, the distal region of the shaft with the outer head profile is formed in a split manner, at least one of the sections of the shaft arising from the split is provided with an oblique contact member and the bushing is provided with a contact ring which acts upon the oblique contact member(s), whereby through a rotation of the bushing relative to the shaft, the section of the shaft provided with the oblique contact member is split off from the other part, by clamping the inner profile recess with the outer profile head of the shaft. In particular the screwdriver can be arranged in such a way, that by turning the bushing relative to the shaft, the section of the shaft provided with the oblique contact member is pulled away from the other part, by clamping the inner profile recess with the outer profile head.

According to a further exemplary embodiment, a screwdriver for a multi-sided hollow screw head is developed, which comprises a shaft and an outer multi-sided head, designed in a manner which corresponds to the inner multi-sided recess of the inner multi-sided screw, whereby the screwdriver is designed with a screwable bushing that receives the shaft, whereby the distal region of the shaft is formed in a split manner in a symmetry plane with the outer multi-sided head, whereby the two split halves of the shaft are provided with oblique contact members arranged to lie opposite each other, whereby the bushing is provided with a contact ring which acts upon the oblique contact member. By turning the bushing relative to the shaft, the separated halves of the shaft are pulled away from each other by clamping the inner multi-sided recess with the multi-sided head. In particular the screwdriver can be arranged in such a way, that by turning the bushing relative to the shaft, the section of the shaft provided with the oblique contact member is pulled away from the other part, by clamping the inner profile recess with the outer profile head.

According to a further exemplary embodiment, a screwdriver for an inner profile screw is developed, which comprises a shaft and an outer head profile designed in a manner which corresponds to the inner profile recess of the inner profile screw, whereby the distal region of the shaft with the outer head profile, made from an elastic material, is formed in a split manner, and an outer surface of the section of the outer head profile is thickly formed, and the section next to the insertion in the inner profile recess of the screw elastically converges on the other section as the gap reduces, and gets elastically clamped in the inner profile recess. Preferably, one section can be provided with an oblique contact member, and the other can be provided with a bushing designed with a corresponding oblique contact member, whereby a rotation of the bushing in the direction of the insertion of the outer head profile in the inner profile recess produces alignment of both of the sections of the shaft with each other, and a rotation of the housing in the opposite direction causes the outer head profile to be clamped in the inner profile recess.

The split distal region of the shaft can be formed as removable.

The plane in which the gap runs can be a symmetry plane, however the gap plane preferably lies eccentrically, i.e. the shaft is asymmetrically split.

The profile can be a multi-sided profile but also a Torx or Torx Plus-profile (hexalobular internal driving feature).

BRIEF DESCRIPTION OF THE DRAWINGS

The invention is hereafter explained according to a design example of the invention expressed in drawing which shows.

DETAILED DESCRIPTION

Figure 1:
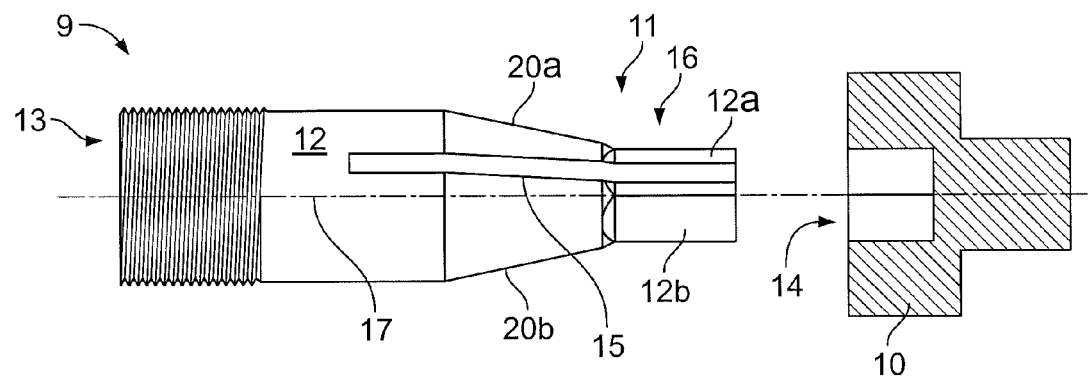
FIG. 1 is an inner profile screw, shown in section view, and the distal end of a shaft of a screwdriver with a tip with an outer head profile.

As shown in FIGS. 1-8, a screwdriver 9 serving to hold and turn an inner profile screw 10 comprises a shaft 12 and a tip outer profile 16 formed at a distal end 11 of the shaft 12, which corresponds to an inner profile recess 14 of the inner profile screw 10. In particular, the inner profile screw 10 can be formed as an inner multi-sided recess, which corresponds to an inner multi-sided screw.

Figure 2:
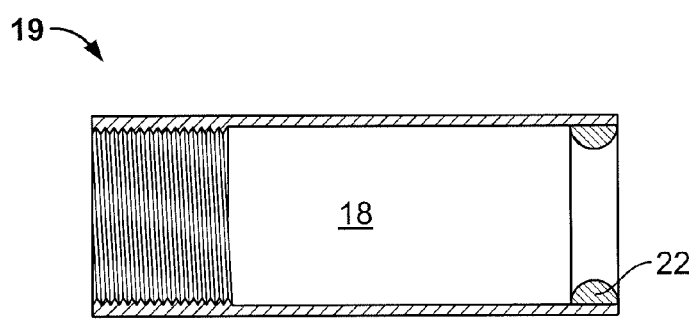
FIG. 2 is a bushing configured to be mounted on to the shaft.
Figure 3:
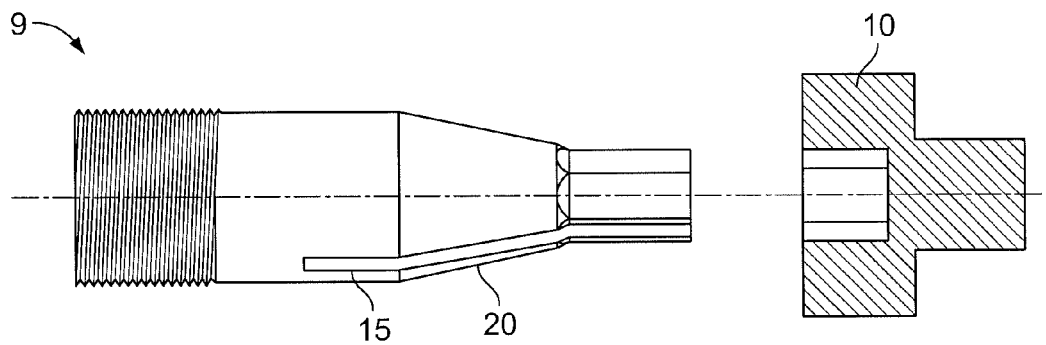
FIG. 3 is the inner profile screw and screwdriver of Fig. 1 rotated by approximately 90°.
Figure 4:
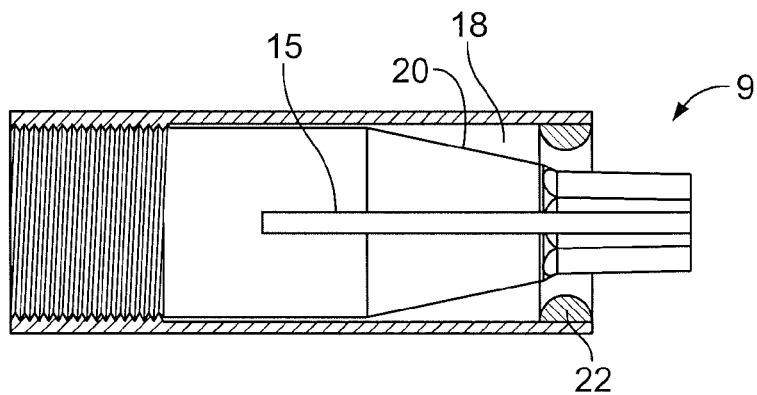
FIG. 4 is the screwdriver of FIG. 1 engaged with the bushing of FIG. 2.
Figure 5:
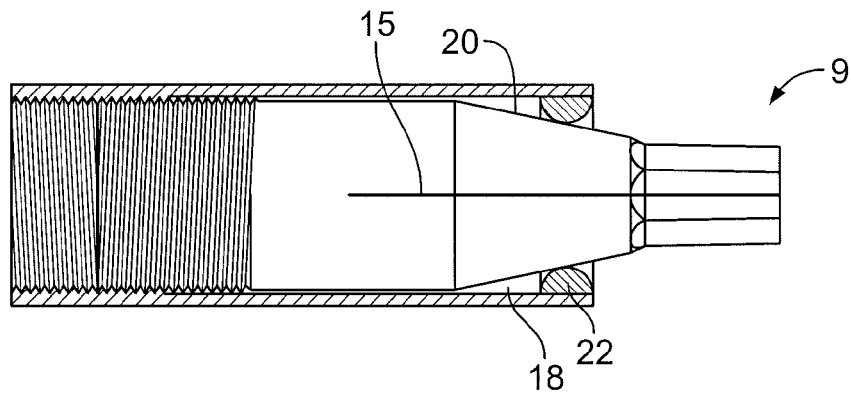
FIG. 5 is another view of the screwdriver of FIG. 1 engaged with the bushing of FIGS. 2.
Figure 6:
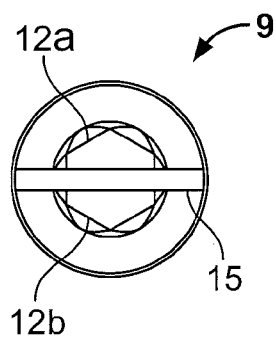
FIGS. 6-8 are end views of different embodiments of the screwdriver of FIG. 1.

On the shaft 12, whose distal end 11 with the tip outer profile 16 is formed in a split manner to include split sections 12a and 12b separated by a slot 15, a housing or bushing 18 shown in FIG. 2 is attached, such that the tip outer profile 16 can extend through a distal portion 19 of the bushing 18, as shown in FIGS. 4 and 5.

In particular, the bushing 18 can be formed to screw onto shaft 12, as shown in FIG. 1.

Both of the split sections 12a, 12b of the tip outer profile 16 of the shaft 12 are provided with an oblique contact member 20a, 20b, respectively, which are angled with respect to the longitudinal axis 17 of the screwdriver 9. The bushing 18 is provided with a contact ring 22 along an inner surface of its distal portion 19 which can act upon the oblique contact members 20a, 20b. By moving the bushing 18 relative to the shaft 12 towards the distal end 11 of shaft 12, the contact ring 22 resets the oblique contact member 20 allowing the split sections 12a, 12b of the tip outer profile 16 of the shaft 12 to be pulled away from each other or otherwise allowing sections 12a, 12b to extend away from each other, as a result of the elasticity of their material, thereby clamping the inner profile recess 14 of the inner profile screw 10. By axially displacing the bushing 18 towards the proximal end 13 of shaft 12, the contact ring 22 again resets the oblique contact members 20a, 20b, the split sections 12a, 12b of the tip outer profile 16 are pressed back together, such that the clamping between the inner profile recess 14 of the inner profile screw 10 and the tip outer profile 16 of the screwdriver 9 is reduced. This allows the axial displacement to be carried out by means of a rotation of the bushing 18 opposite to the shaft 12, in particular when the bushing 18 is formed as screwable with the shaft, i.e. both of the elements comprise a complementary thread.

Figure 7:
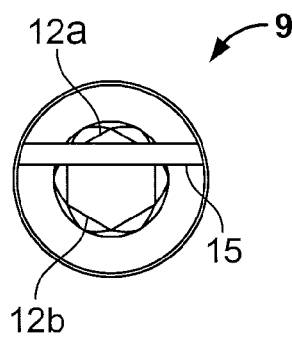
Figure 8:
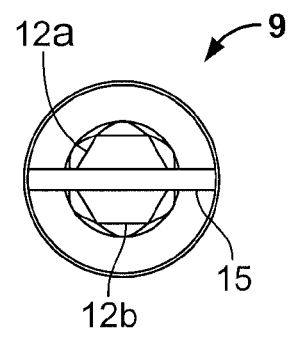

The distal end 11 of the shaft 12 with the tip outer profile 16 and multi-sided head can be formed in a split manner to include split sections 12a and 12b disposed about symmetrical plane, which lies parallel to two faces of the multiple sides of the multi-sided head, as shown in FIG. 8. Preferably however, the distal end 11 of the shaft 12 is asymmetrically, i.e. eccentrically, split as shown in FIG. 7. Such an asymmetric split can in particular lead to one of the two sections of the shaft 12 (e.g., sections 12a, 12b) being smaller than the other section of the shaft 12, i.e. the two sections exhibit different cross-sectional areas. For example, the smaller of the two sections can exhibit a cross sectional area which comprises one-third to one-eighth of the cross sectional area of the other. Such an asymmetric separation can have the advantage that the force, i.e. from exertion of the torque on the two sections of the shaft by use of the screwdriver 9, prevents breakage of the shaft or at least delays it, i.e. a fracture only occurs when a larger torque is exercised.

Furthermore, the two split sections 12a, 12b of the shaft 12 can be provided with oblique contact members 20a, 20b, respectively, arranged to lie opposite one another and the bushing 18 can be provided with a contact ring 22 acting on one of the oblique contact members 20. With a rotation of the bushing 18 relative to the shaft 12 toward the distal end 11, in the case of a screwable bushing 18, the split sections 12a, 12b of the shaft 12 are separated and pulled or otherwise allowed to extend away from each other, as a result of the elasticity of the material, thereby clamping the inner profile recess 14 of the inner profile screw 10. By rotating the bushing 18 toward the proximal end 13 of shaft 12 in such a manner that the contact ring 22 again contacts the oblique contact members 20a, 20b, the separated halves, or split sections 12a, 12b, of the tip outer profile 16 are pressed back together.

In an alternative embodiment (not shown), the distal region of the shaft 12 with the outer multi-sided head 16 is formed in a split manner in a symmetry plane, in a corresponding manner. One half of the split is cut at a lower angular degree (in the absence of a force) than the other half of the split. The two halves are aligned by bringing in the split outer multi-sided head into the inner multi-sided recess of the screw 10 and clamping themselves as a result of the elasticity of the material of the outer multi-sided head.

In a further alternative embodiment, one of the two separated sections 12a, 12b of the shaft 12 is provided with an oblique contact member 20 and the bushing 18 is provided with a contact ring 22 acting on one of the oblique contact members 20. With a rotation of the bushing 18 relative to the shaft 12 toward the distal end 11, the split sections 12a, 12b of the shaft 12 are separated and pulled or otherwise allowed to extend away from each other, as a result of the elasticity of the material, thereby clamping the inner profile recess 14 of the inner profile screw 10. With a rotation of the bushing 18 toward the proximal end 13 of shaft 12 in such a manner that the contact ring 22 again contacts the oblique contact member 20, the separated sections 12a, 12b of the tip outer profile 16 are pressed back together.

In an alternative embodiment (not shown), the distal region of the shaft 12 with the outer head profile 16 is formed in a split manner. One section of the split is cut at a lower angular degree (in the absence of a force) than the other section of the split. The two halves are aligned by bringing in the split outer profile head into the inner recess profile of the screw 10 and clamping themselves as a result of the elasticity of the material of the outer head profile. Thereby, as described in the previous embodiments, a bushing may be provided, by which rotation of the sections with respect to one another enables alignment, and so enables an insertion of the outer multi-sided head into the inner multi-sided recess. By turning back the bushing, the sections again want to engage the cut final position, thereby clamping themselves in the inner profile recess.

In a further embodiment, an outward slanting side of one section of the outer multi-sided head is thickly formed, the section itself moves nearer to the other section by insertion into the inner multi-head profile, causing reduction of the gap width, causing a clamping-pressure to be exerted on the corresponding side of the inner multi-sided recess.

In each of the above examples, the bushing can thereby—preferably via a torque limiter—be loaded with a defined force, so that the application of a defined clamping force independent of tolerances is assured. Furthermore, in each of the above described examples, the shaft can not only be simply formed in a split manner, but the separation or split can be formed such that one section of the distal end of the shaft is removed, i.e. a groove or a notch in the cross sectional area of the shaft is formed. In other words, the cross-sectional area of the two sections no longer completely reproduce the inner profile of the screw, but provide a total cross section which is smaller than the cross-sectional area of the inner profile of the inner profile screw. Such a recess may, by insertion of the screwdriver, increase the breaking resistance of the shaft of the screwdriver.

In particular it should be noted that all of the above, described in connection with characteristics of an embodiment, could also be combined with characteristics of other embodiments.

The invention claimed is:

1. A screwdriver for an inner profile screw comprising:
   an axially extending shaft and a tip at a distal shaft region having a profile formed in a manner which corresponds to an inner profile recess of an inner profile screw, and
   a moveable bushing,
   whereby the tip at the distal shaft region of the shaft has an outer profile formed in a split manner to form at least two sections and the shaft is received within the moveable bushing,
   whereby at least one of the at least two sections of the tip is provided with an oblique contact member,
   whereby the bushing is provided with an inwardly extending contact ring disposed around a circumference of the bushing and configured to act upon the oblique contact member upon movement in an axial direction along the shaft, and
   whereby through movement of the bushing relative to the shaft toward the tip, the at least two sections of the tip are allowed to deflect away from one another, clamping the inner profile recess with the tip.

2. The screwdriver according to claim 1,
   whereby the shaft is formed from an elastic material;
   whereby the bushing is formed as a housing which is screwable with the shaft;
   and whereby the movement of the bushing is a rotation of the bushing relative to the shaft.

3. The screwdriver according to claim 1 or 2, whereby a plane of a gap forming the split at the tip at the distal region of the shaft is arranged parallel and eccentrically to a central shaft axis.

4. The screwdriver according to claim 1,
   whereby the inner profile screw is an inner multi-sided screw;
   whereby the outer profile of the tip is formed as an outer multi-sided head;
   whereby the bushing is formed as a bushing which screws onto the shaft;
   whereby the outer multi-sided head is formed in a split manner in a symmetry plane, and the two split halves of the shaft are provided with oblique contact members lying opposite to each other; and
   whereby the movement of the bushing is achieved by rotation of the bushing relative to the shaft.

5. The screwdriver according to claim 4, whereby the shaft is split parallel to two faces of multiple sides of the outer multi-sided head.

6. A screwdriver for a screw having a drive socket comprising:
   an axially extending shaft with a bifurcated tip having two sections, the tip having a cross-sectional profile for insertion into a cross-sectional profile of the drive socket, the shaft having a tapered section adjacent the bifurcated tip; and
   a bushing mounted on an outer surface of the shaft for axial movement therealong, the bushing having an inwardly extending protrusion disposed around a circumference of the bushing for engaging the tapered section on the shaft upon movement in the axial direction along the shaft,
   wherein when the bushing is moved in the axial direction from the tapered section toward the bifurcated tip, the two sections of the tip are allowed to expand apart from one another.

7. The screwdriver according to claim 6,
   whereby the shaft is formed from an elastic material;
   whereby the bushing is formed as a housing which is screwable with the shaft;
   and whereby the movement of the bushing is a rotation of the bushing relative to the shaft.

8. The screwdriver according to claim 6,
   whereby the screw is an inner multi-sided screw;
   whereby the cross-sectional profile of the tip is formed as an outer multi-sided head;
   whereby the bushing is formed as a bushing which screws onto the shaft;
   whereby the outer multi-sided head is formed in a split manner in a symmetry plane, and the two split halves of the shaft are provided with oblique contact members lying opposite to each other; and
   whereby the movement of the bushing is achieved by rotation of the bushing relative to the shaft.

* * * * *